United States Patent [19]

Taylor

[11] Patent Number: 5,411,087
[45] Date of Patent: May 2, 1995

[54] SOIL SAMPLER

[76] Inventor: Byron D. Taylor, 110 Bonaventure Pl., Nashville, Tenn. 37205

[21] Appl. No.: 187,645

[22] Filed: Jan. 27, 1994

[51] Int. Cl.⁶ .............................................. E21B 49/08
[52] U.S. Cl. .................................. 166/264; 73/863.11; 73/864.73; 166/169; 175/20; 175/58
[58] Field of Search ............... 166/264, 370, 169, 303; 175/20, 58; 73/863.11, 863.23, 864.35, 864.73

[56] References Cited

U.S. PATENT DOCUMENTS

| | | | |
|---|---|---|---|
| 2,141,261 | 12/1938 | Clark | 166/264 X |
| 2,210,546 | 8/1940 | Hassler | 166/264 X |
| 3,857,289 | 12/1974 | Wine et al. | 175/58 X |
| 3,878,906 | 4/1975 | Guest | 175/405 |
| 3,955,631 | 5/1976 | Kostylev et al. | 175/20 |
| 4,498,547 | 2/1985 | Herkness, II | 175/244 |
| 4,549,612 | 10/1985 | Cushing | 175/20 |
| 4,556,114 | 12/1985 | Ryan | 175/20 |
| 4,576,498 | 3/1986 | Rassieur | 403/24 |
| 4,907,659 | 3/1990 | Ludwig | 175/20 |
| 5,010,776 | 4/1991 | Lucero et al. | 73/863.23 |
| 5,035,149 | 7/1991 | Wierenga | 73/863.23 |
| 5,101,917 | 4/1992 | Abdul et al. | 175/253 |
| 5,147,561 | 9/1992 | Burge et al. | 166/264 X |
| 5,150,622 | 9/1992 | Vollweiller | 73/864.74 |
| 5,337,838 | 8/1994 | Sorensen | 166/264 X |

*Primary Examiner*—Hoang C. Dang

[57] ABSTRACT

A soil sampler for insertion into a pilot hole in the earth to extract contaminants in a vapor state. The sampler has an axially forward projection and an axially rearward projection that define a volume together with the body of the sampler and the wall of the pilot hole. Steam passes into the sampler so as to heat a portion of the sampler near the volume so as to volatize the contaminants. The sampler exerts a vacuum on the volume to extract the gaseous contaminants into an analyzer assembly.

12 Claims, 2 Drawing Sheets

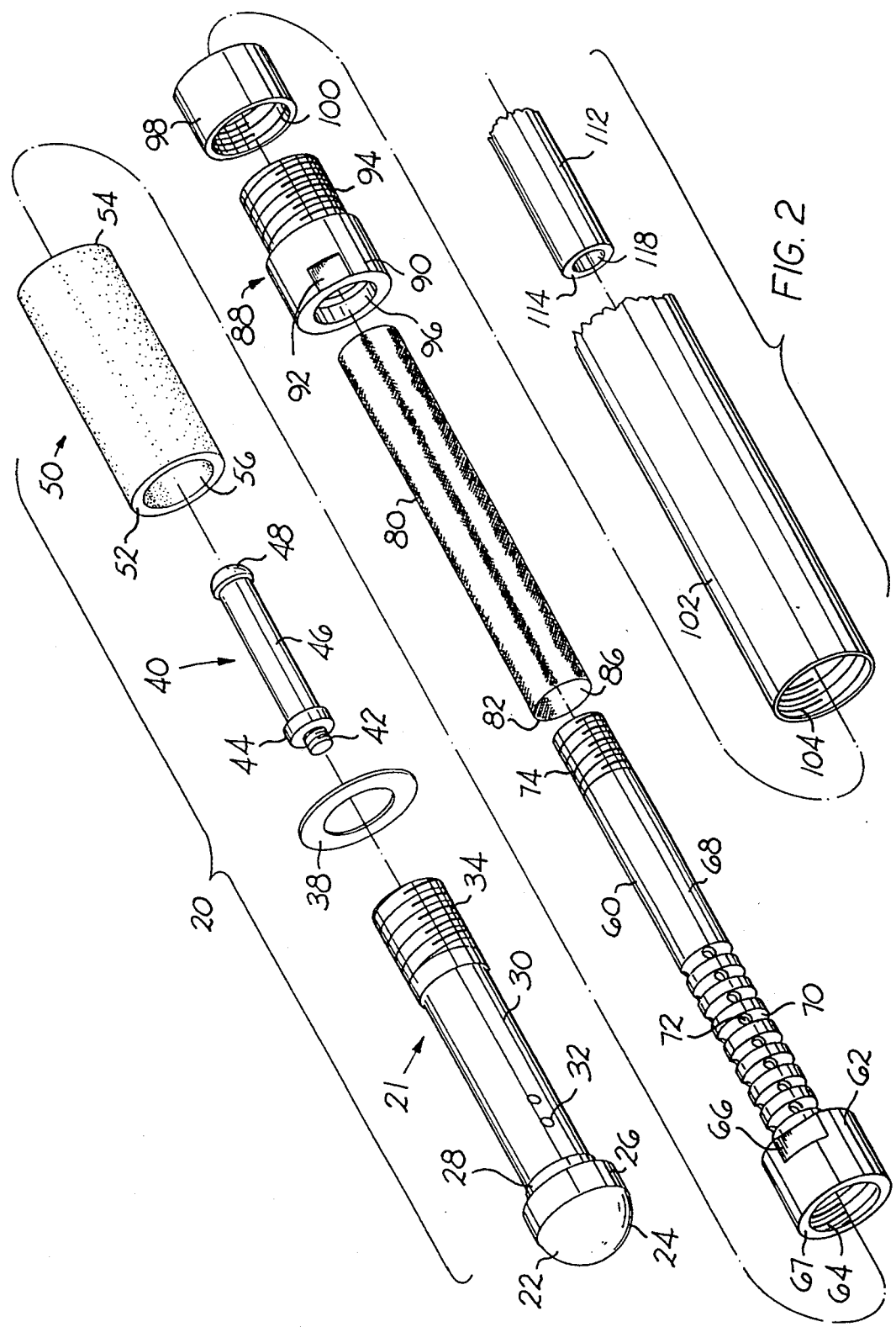

SOIL SAMPLER

BACKGROUND OF THE INVENTION

The invention pertains to soil samplers, and in particular, to a soil sampler inserted into a pilot hole in the ground and positioned to a selected depth so as to volatize contaminants, and thereafter accumulate and transport contaminants to the surface for analysis.

It was not until 1975 that soil sampling was first attempted as a means to detect and trace ground contaminants. These early applications involved inserting pipes one to one-and-a-half feet into the ground to measure the evolution of both hydrocarbon and non-hydrocarbon gases. Since that time, the concept has taken two somewhat different directions in application; namely, in place passive soil gas sampling devices and mechanically inserted active soil gas sampling ground probes. The mechanically inserted sampling probes have involved large and small sampling approaches and several variations on sample extraction and analysis.

Numerous applications have involved auguring bore holes into the soil, placing a hollow breathing tube into the bore hole and backfilling with the cuttings. Sampling tips for obtaining soil gas samples range from glass tubing with flared openings to porous/sintered bronze cups and various perforated probe tips. These applications all demonstrated the same disadvantage; namely, that the auguring of the bore hole altered the soil gas composition and caused the loss of many of the gases of interest which changed relative as well as overall concentrations. The procedure required several days for the disturbance to equilibrate, which left numerous questions as a result of the variability of gaseous movements through the undisturbed soil. Furthermore, due to the absence of a reliable seal between the sampling point or probe shaft and the atmosphere, the dilution of the gaseous samples was found to cause false negatives and unreliable relative concentration results. Obviously, the above drawbacks detracted from the credibility of any analysis of these soil samples.

Alternative techniques intended to correct the two major deficiencies of the previous method were developed and took the form of mechanically inserting probes with sacrificial penetration tips or perforated well points to the desired depth. The expense involved with sacrificial penetration tips has been a drawback to that approach. This procedure minimized the disturbance of the soil matrix, caused no significant release of soil gases, and provided an improved natural seal between the sampling point and probe shaft and the surface atmosphere. Variations of this type of "breathing" soil probe have been widely applied. The principal limitation of the perforated well-point method was the blinding or clogging of the sample ports with soil during the insertion process. This led to the development of several types of closed well-points which were opened mechanically upon reaching the desired depth by extracting the insertion casing.

Early researchers found the mechanical insertion method to be preferable to the augured insertion technique and more reliable in obtaining accurate, reproducible soil gas samples. However, some of these commercially available well-points continue to experience problems in opening as a result of the high compression experienced during the insertion process. The principal limitation of this process was the relatively high volume of gas within the interior of the probe that needed to be extracted prior to obtaining a representative soil gas sample. Also, dilution of the sample becomes a problem when the volume of the gas within the probe is relatively large. Structural demands required that the probe shafts be relatively heavy to withstand the rigors of the insertion process which limited the freedom to physically down-size the casing shafts. This limitation was overcome by redesigning the well-points to allow for the attachment of laboratory tubing between the well-point and the surface where the sample is withdrawn. The benefit of this process was that a smaller sample volume was necessary to purge the system, and consequently, a sample more representative of the interstitial gases was obtained at the surface sampling point.

The various methods of manually and mechanically inserting the probes range from manual drop-hammers, to hydraulic and mechanical impact hammers, to hydraulic penetration devices. The insertion of the sample point by driving the unit with an impact/percussion hammer on the upper end of the connecting shaft results in greater by-passing of diluting atmospheric gases during sampling. The cause of this problem is the compacting of the soil which contacts the probe shaft during insertion by the vertical impact/force being converted to lateral motion by the combining forces of the impact and the counterpoising resistance to penetration and friction.

Sample extraction techniques have ranged from passive, atmospheric movement of the soil gases to the surface, to low and high vacuum extraction methods. The passive process was based on the natural diffusion of gases from higher concentrations in the soil to the sampling ports in the well-point. Since this process was based on the natural concentration gradient, researchers often found that tight, clayey soils were too restrictive to the natural movement of soil gases. This technique also required considerable time for soil gases to collect within the sampling probe for final drawing for analysis. Therefore, it was limited to relatively high concentrations of volatile contaminants.

The application of low vacuum to the sampling probe was the first attempt to address this limitation. This reduced the time required for the accumulation of soil gases within the sampling probe but did not materially affect the migration of gases through tight soils to the well-point. High vacuum extraction processes were later developed to increase extraction efficiency. However, this technique required the development of gas cleaning systems at the surface since ground water and soil particles were often drawn through the probe. Also, structural improvements to the system were necessary to accommodate the larger pressure differential. A significant additional advantage of the high vacuum systems was the reduction of the partial gas pressure in the sampling zone of the soil causing heavier and more complex molecules to volatilize at the reduced pressures.

Analytical methods used to process the extracted sample have included colormetric gas tubes, gas bag samplers, carbon adsorbing tubes, combustible gas indicators and gas chromatographs. Portable, laboratory quality flame- and photo-ionization detector/gas chromatographs have provided a mechanism whereby the extracted soil gas samples can be separated into their various components and can be analyzed on-site. Gas chromatography has utilized both flame-ionization detectors and photo-ionization detectors, as well as electron capture and far-ultraviolet detectors. The most common processes deliver the sample to the analytical device by the use of gas tight syringes to extract the gas sample, and most recently by extracting gas samples directly from the vacuum pump exit stream. This second procedure is more expeditious but requires care so as not to over pressurize the analytical instrument with exit gases from the vacuum pump. Also, accuracy in measuring the flow of a moving stream as well as incorporating effective gas cleaning devices for removing moisture and soil particles are necessary in order to obtain a representative sample for analysis.

Certain commercially available, closable well points have exhibited a tendency to jam with soil under repeated opening and closing while in the subsurface soil regime. The repeated opening and closing of the well points which is necessary when readings are taken during insertion can result in either the blinding or clogging of the sampling ports or the jamming of the protecting shroud itself restricting the ability to open the point when reaching the succeeding test elevation.

Chemical factors affecting the soil vapor assessment process include the variations in vapor pressures and boiling points of the compounds of interest themselves, and the appropriateness of the detection and analytical devices employed in relation to the contaminant compounds. The relationship between the various soil conditions can be characterized by the following formula.

$$C_g/C_t = 1/((P_g K_{oc} f_{oc}/K_h) + (O/K_h + a))$$

where:
$C_g/C_t$ = Relative Vapor Concentration. [(mg/cm$^3$• air)/(mg/cm$^3$• soil)]
P = Bulk Density (g/cm$^3$)
$K_{oc}$ = Organic Carbon-Water Partition Coefficient (cm$^3$/g)
$f_{oc}$ = Fraction of organic carbon content (g/g)
$K_h$ = Henry's Constant [unitless ratio]
O = Volummetric Moisture Content (cm$^3$/cm$^3$)
a = Volummetric Air Content (cm$^3$/cm$^3$)

Research into the behavior of wet and dry gaseous compounds and the laws affecting gases have provided a number of constants and predictable reactions for the contaminant compounds commonly found in soil matrices. Soil vapor contaminant assessment is possible since vapors indicative of contamination resulting from volatile organic compounds are present within the voids of the soil interstices. These contaminant vapors evaporate from contaminated water or result from non-aqueous phase liquids (NAPL) released in the vadose (unsaturated) zone of the soil.

Research has shown that both Henry's and Raoult's Laws are important in understanding the equilibrium of contaminant concentrations resulting from volatilization of aqueous and non-aqueous phase liquids. Raoult's law describes the equilibrium vapor phase concentrations above a dissolved contaminant in higher concentrations.

Raoult's Law: $C_v = X C^°_v$ where:
$C_v$ = concentration in vapor phase (i.e., the vapor in soil interstices) (mmHg)
X = mole fraction of compound in solution
$C^°_v$ = concentration in vapor phase above pure liquid (i.e., vapor pressure) of the component of interest (mmHg)

Henry's Law describes the equilibrium vapor phase concentration above water containing an organic solute at low concentrations.

Henry's Law: $C_v = K_h C_w$ where:
$C_v$ = concentration in vapor phase
$K_H$ = Henry's Law coefficient
$C_w$ = concentration in aqueous phase Based on Raoult's and Henry's laws and the vapor pressures of various organic compounds, it is clear that not all contaminants can be detected using soil vapor assessment techniques. The compounds of interest must be sufficiently volatile to enter the vapor phase in sufficiently high concentrations to be extracted and detected and must have an adequately low aqueous solubility so that they do not remain in aqueous solution. Currently, soil vapor analysis are limited by the vapor pressure and Henry's Law constant (i.e., vapor pressure and aqueous solubility) for the compounds of interest. Generally, for the process to be reliable, the contaminant compounds should have a vapor pressure of at least 1.5 mmHg at 25° C. and a Henry's Law constant of at least 0.1 kPam$^3$ per mole. The list set out below is a partial listing of compounds that are amenable for soil vapor assessments based on current procedures.

| | VAPOR PRESSURE (mmHg) | HENRY'S LAW CONSTANT (kPa M3/mole) |
|---|---|---|
| Benzene | 95 | 0.6 |
| Bromoform | 5 | 0.06 |
| Bromomethane | 1300 | 0.5 |
| Carbon Tetrachloride | 15 | 2.0 |
| Chlorobenzene | 12 | 0.4 |
| Cloroethane | 700 | 0.2 |
| Chloroform | 190 | 0.4 |
| Chloromethane | 3750 | 1.0 |
| 1,2 Dichlorobenzene | 1.5 | 0.2 |
| 1,3 Dichlorobenzene | 2 | 0.4 |
| 1,1 Dichloroethane | 500 | 15.0 |
| 1,2 Dichloroethene | 700 | 0.1 |
| 1,1 Dichloroethene | 200 | 0.6 |
| trans-1,2 Dichloroethene | 300 | 0.6 |
| 1,2 Dichloropropane | 50 | 0.4 |
| cis-1,3 Dichloropropene | 40 | 0.2 |
| Ethylbenzene | 9 | 0.8 |
| Methylene Chloride | 350 | 0.3 |
| 1,1,2,2 Tetrachloroethane | 5 | 0.05 |
| Tetracholorethene | 15 | 2.0 |
| Toluene | 28 | 0.7 |
| 1,1,1 Trichloroethane | 100 | 3.0 |
| 1,1,2 Trichloroethane | 25 | 0.1 |
| Trichloroethene | 50 | 0.9 |
| Vinyl Chloride | 2200 | 50.0 |
| o-xylene | 6 | 0.5 |
| m-xylene | 8 | 0.7 |
| p-xylene | 8 | 0.7 |

Several researchers have attempted to change the subsurface conditions in an attempt to expand the range of compounds amenable to the soil vapor assessment process. One researcher reported that the detectability of organic compounds depends upon their ability to volatilize into the porous spaces of the soil and that most contaminants volatize either directly from the soil or from dissolved aqueous phase. Since the temperature of the subsurface soil below one meter reflects the mean ground water temperature of 65° F. or less, normal low vacuum gas extraction is generally limited to those compounds having standard condition boiling points of less than 150° F. and vapor pressures greater than 0.002 atmospheres.

The capacity to detect organic compounds by soil vapor techniques depends upon contaminant volatility. Soil vapor concentrations are related to two governing systems: water phase and non-aqueous product phase. Raoult's and Henry's laws are commonly used to understand equilibrium vapor concentrations governing the volatilization from liquids. Therefore, the ability to manipulate or change the variables in these equations will allow for expansion of the range of compounds suitable and detectable by soil vapor extraction techniques. The theory of the interaction between soil temperature and the role of pressure has not been fully developed. However, research and experience have empirically established without question that elevating sub-surface soil temperature and reducing the local atmospheric pressures will result in a broadened spectrum of extractable compounds. It has also been established that the release of volatile gases form a soil matrix is influenced by the moisture content of the soil. Gases adsorb more strongly to dry soil particles and conversely will desorb to a greater extent from moist particle surfaces.

Experience with in situ vacuum extraction has shown that moist soils are dried by the vacuum extraction process. Some decrease in the release of volatile organic compounds will result due to enhanced adsorption between the hydrocarbon molecules and the soil particle surfaces due to drying as extraction progresses. This increased adherence can be reversed or avoided by maintaining adequate soil moisture during the extraction process. This phenomenon is mathematically described by the Relative Vapor Concentration Formula. By applying and moisture heat to the sub-surface soil conditions, ensuring that drying of the soil matrix does not occur, and reducing the ambient pressure in the zone of extraction, compounds with boiling points of up to 400° F. and 0.007 atmospheres vapor pressure can be suitable for soil vapor analysis.

SUMMARY OF THE INVENTION

It is a principal object of the invention to provide an improved soil sampling device inserted into a pilot hole in the ground.

It is another object of the invention to provide an improved soil sampling device inserted into a pilot hole in the ground that is positioned at a selected depth so as to volatize the contaminants in the test region of the earth.

It is still another object of the invention to provide an improved soil sampling device inserted into a pilot hole the ground that minimizes the loss of any contaminant vapors.

It is still another object of the invention to provide an improved soil sampling device inserted into a pilot hole in the ground that reduces the dilution of gas samples.

It is another object of the invention to provide an improved soil sampling device inserted into a pilot hole in the ground that does not use percussion impacts to drive the device into the ground.

BRIEF DESCRIPTION OF THE DRAWINGS

The following is a brief description of the drawings that form a part of this patent application:

FIG. 2 is an exploded perspective view of the specific embodiment of the invention.

DETAILED DESCRIPTION OF THE SPECIFIC EMBODIMENT

Figure 1:
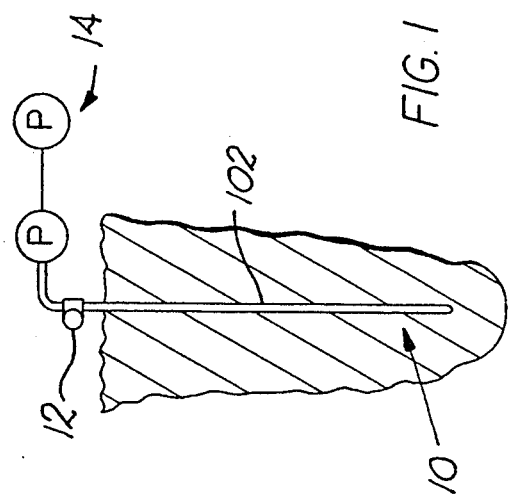
FIG. 1 is a schematic view illustrating the soil sampling device in a bore hole and connected to the analyzer.
Figure 3:
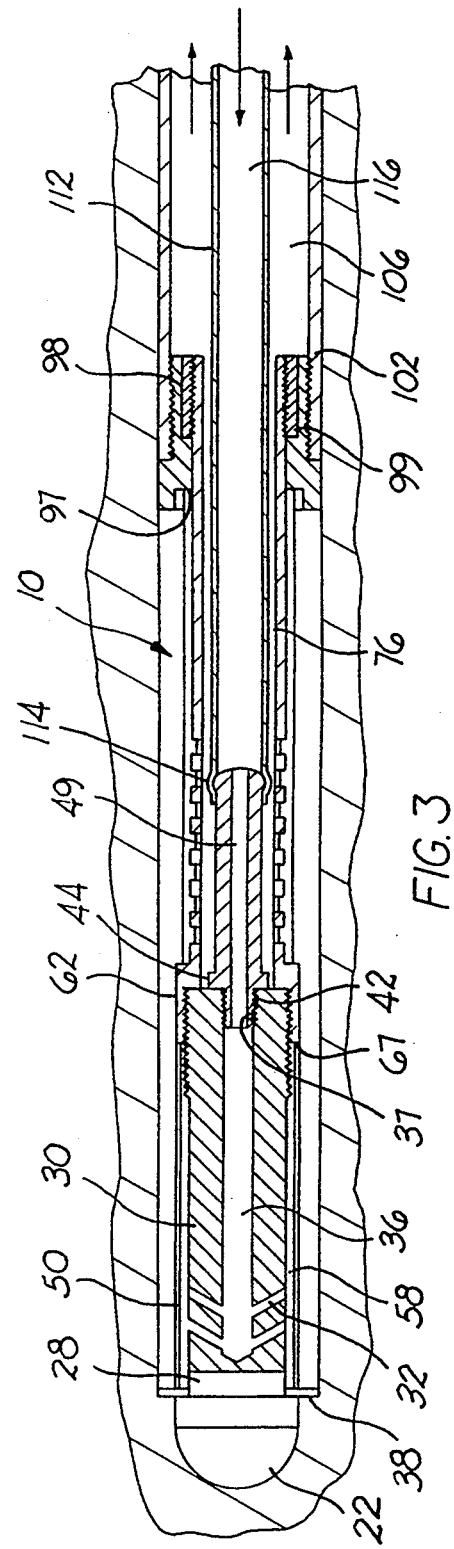
FIG. 3 is a cross-sectional view of the specific embodiment of the invention in an assembled condition (extended) and inserted in a bore hole.

Referring to FIGS. 1 through 3, the specific embodiment of the soil sampling device of the invention is generally referred to as 10. In FIG. 1, soil sampler 10 connects, via tube 102 and through a valve 12, to an analyzer assembly 14. The analyzer assembly 14 can take on many forms. The specific analyzer presently preferred by applicant is the Model 311D made by HnU Systems Inc. of 160 Charlemont Street, Newton Highlands, Mass. 02161-9987. Referring to FIGS. 2 and 3, soil sampler 10 has a distal section shown in brackets as 20 in FIG. 2. Distal section 20 includes an axially forward member generally designated as 21. Axially forward member 21 includes an axially forward nose 22 which has a generally semi-spherically shaped section 24, an integral cylindrical section 26 (which is axially rearwardly of the semi-spherical section 24), and a shoulder 28.

Axially forward member 21 further includes a shank 30 that projects axially rearwardly from the nose 22. Shank 30 includes a plurality of radial ports 32 contained therein which communicate with a central longitudinal bore 36. The axially rearward end of the shank 30 includes external threads 34. The axially rearward end of the bore 36 includes internal threads 37. The distal section 20 also includes a sacrificial washer 38, the position and function of which will be described hereinafter.

The distal section 20 further includes a tube connector 40 that includes external threads 42, a collar 44, a shank 46 and a nipple 48. Tube connector 40 further includes a bore 49. The distal section 20 includes a rigid porous cylindrical sleeve 50 made from sintered metal. Sleeve 50 has axially forward and rearward ends 52 and 54 and a central passageway or volume 56 therein. The preferred material for the sintered metal sleeve is 316L stainless steel 10 microns in size.

The mediate section includes a mediate member 60 having a cap 62 with internal threads 64 and a notch 66. A mediate shank 68 projects axially rearwardly from the cap 62. Mediate shank 68 contains external grooves 70 which lead into radial holes 72. Holes 72 communicate directly with a central passage 76. Mediate shank 68 further includes external threads 74.

The mediate section further includes a wire mesh cylinder 80 with axially forward and rearward ends 82 and 84, respectively. Cylinder 80 defines a central passage or volume 86 therein. The size of the mesh is such so as to permit the passage of contaminants in their vapor state; yet, prevent passage of particulates, such as, for example, dirt from the pilot hole.

An axially rearward assembly includes a retainer 88 which has an enlarged diameter section 90 that contains a notch 92 and threads 94. The retainer 88 includes a central passage 96. The axially rearward assembly further includes a sleeve 98 with internal threads 100. An elongate tube 102, having internal threads 104, is a part of the axially rearward assembly. A flexible steam tube 112 has opposite forward and rearward ends 114 and 116, respectively. Tube 112 also defines a passage 118 therein.

Referring now to the assembled soil sampler 10, the washer 38 rests on the shoulder 28 of the nose 22. Washer 38 is sandwiched between the shoulder 38 and the axially forward end 52 of the sintered sleeve 50. Sintered sleeve 50 is positioned on the shank 30 of the axially forward member 21 so as to envelope the ports 32. There is annular plenum 58 defined by the shank 30 of the axially forward member 21 and the sleeve 50. Tube connector 40 has the threads 42 received in the threaded portion 37 of the base 36 of the axially forward member 21, so as to connect the tube connector 40 to the axially forward member 21.

The mediate member 60 is connected to the axially forward member 21 in the following fashion. The threads 64 of the cap 62 engage the threads 34 on the shank 30 of the axially forward member 21. The axially forward edge 67 of the cap 62 abuts against the rearward end 54 of the sintered sleeve 50 so as to maintain the sintered sleeve 50 between the washer 38 and the cap 62.

Mesh screen 80 is positioned over mediate shank 68 so as to envelope grooves 70 and holes 72.

Retainer 88 includes an internal shoulder 97 which rests upon the rearward end 84 of the screen 80. Retainer 88 further includes another internal shoulder 99 which faces axially rearwardly. The threads 100 of sleeve 98 engage the threads 74 of the mediate member 60 in such a fashion so that the forward edge of collar 98 abuts against the internal shoulder 99 of retainer 88 to retain the retainer 88 to the mediate member 60.

The threads 104 of tube 102 engage threads 94 of retainer 88 so as to connect the tube 102 to retainer 88. The rearward end of tube 102 connects to a vacuum source.

Flexible tube 112 connects at the forward end thereof to tube connector 40 at nipple 48. Flexible tube 112 connects at its rearward end to a source of steam.

In operation, steam is injected through flexible tube 112 so that steam passes through the passage 118, the bore 49 of the tube connector 40, and the bore 36 of the axially forward member 21. The steam then passes through the ports 32 and into the plenum 58. The heat carried by the steam is removed by the sintered sleeve 50, which essentially acts as a heat sink. The temperature of the sintered sleeve 50 is raised to such a level that the heat volitizes the contaminants in the region of the earth that defines the pilot hole near sintered sleeve. These contaminants then vaporize into a gaseous state.

The vacuum drawn via the tube 102 causes a vacuum on the volume. The vacuum causes the gases to pass through the screen 80, the holes 72 and into passage 76. The gases then move axially rearwardly through passage 76 into the volume of tube 102 and are carried to the analyzer assembly 14 for analysis.

The scope of the present invention is to be defined by the following claims.

What is claimed is:

1. A soil sampling device comprising:
   an axially forward member having a nose with an axially rearwardly facing shoulder, said axially forward member having a forward shank projecting axially rearwardly from said nose, said forward shank having a bore contained therein and at least one generally radially extending port communicating with said bore;
   a washer resting against said shoulder, said washer having a diameter greater than the transverse dimension of said nose;
   a rigid porous member is positioned on said forward shank so as to envelope each one of the ports, said forward shank and said rigid porous member define an annular plenum therebetween;
   a heat hose communicates with said bore so as to supply a heated fluid to said bore which passes through each one of the ports and into said plenum;
   a mediate member having a mediate collar and a mediate shank wherein the mediate shank has a passage and at least one radial hole contained therein;
   a screen is positioned on the mediate shank so as to envelope each one of the radial holes;
   a vacuum supply hose communicates with the surface of the screen through the holes and the passage so as to exert a vacuum at the surface of the screen; and
   an axially rearward assembly including a rearward collar and an elongate tube, the maximum diameter of the rearward assembly being about equal to the diameter of the washer.

2. The device of claim 1 wherein the axially forward member has a plurality of said ports.

3. The device of claim 1 wherein the rigid porous member is made from sintered metal.

4. The device of claim 3 wherein the rigid porous member is made from 316L stainless steel.

5. The device of claim 1 wherein the heated fluid is steam.

6. The device of claim 1 wherein the mediate member has a plurality of the holes.

7. A soil sampling device for being inserted down a borehole in the earth, the device comprising:
   an axially forward member having a radially extending forward projection;
   an axially rearward assembly that includes a radially extending rearward projection;
   said forward projection and said rearward projection define a volume between the earth and the device;
   a fluid means for supplying a heated fluid into the volume so as to volatize selected compounds present in the region of the earth defining the volume into their vapor state; and
   a vacuum means for drawing the vapors out of the volume.

8. The device of claim 7 further including a sintered metal sleeve surrounding the axially forward member.

9. The device of claim 7 wherein the heated fluid is steam.

10. The device of claim 9 wherein said axially forward member contains a central bore and a plurality of ports which communicate with the bore, the ports provide communication between the bore and the volume.

11. The device of claim 10 wherein the fluid means includes source of steam, a tube connected to the axially forward member whereby said tube supplies steam to said bore.

12. A method of sampling an earth formation for contaminants comprising the steps of:
   forming a borehole into the earth;
   inserting a soil sampling device into the borehole;

positioning the soil sampling device at a desired depth in the borehole;

providing the soil sampling device with an axially forward radial projection and an axially rearward radial projection that together with the device and the wall of the borehole define a volume;

introducing a heated fluid into the volume so as to volatize contaminants into the vapor state within the surface region of the borehole that defines the volume; and transporting the contaminant vapors to an analyzer.

* * * * *